US012672907B2

(12) United States Patent
Frame et al.

(10) Patent No.: US 12,672,907 B2
(45) Date of Patent: Jul. 7, 2026

(54) MODULAR DOCKING SYSTEM FOR ELECTROSURGICAL EQUIPMENT

(71) Applicant: Conmed Corporation, Utica, NY (US)

(72) Inventors: Dan Frame, Salt Lake City, UT (US); John Cook, Conifer, CO (US)

(73) Assignee: Conmed Corporation, Utica, NY (US)

( * ) Notice: Subject to any disclaimer, the term of this patent is extended or adjusted under 35 U.S.C. 154(b) by 920 days.

(21) Appl. No.: 17/433,787

(22) PCT Filed: Feb. 26, 2020

(86) PCT No.: PCT/US2020/019821
§ 371 (c)(1),
(2) Date: Aug. 25, 2021

(87) PCT Pub. No.: WO2020/176578
PCT Pub. Date: Sep. 3, 2020

(65) Prior Publication Data
US 2022/0133385 A1     May 5, 2022

Related U.S. Application Data

(60) Provisional application No. 62/810,486, filed on Feb. 26, 2019.

(51) Int. Cl.
A61B 18/00          (2006.01)
A61B 18/12          (2006.01)

(52) U.S. Cl.
CPC ............................... A61B 18/1206 (2013.01);
A61B 2018/00178 (2013.01); A61B 2218/008 (2013.01);
(Continued)

(58) Field of Classification Search
None
See application file for complete search history.

(56) References Cited

U.S. PATENT DOCUMENTS

| | | | |
|---|---|---|---|
| 5,601,445 A | 2/1997 | Schipper et al. | |
| 10,117,702 B2 | 11/2018 | Danziger et al. | |

(Continued)

FOREIGN PATENT DOCUMENTS

| | | |
|---|---|---|
| JP | 1994-178780 A2 | 6/1994 |
| JP | 2007-123264 A2 | 5/2007 |

(Continued)

OTHER PUBLICATIONS

Stephanie Junek, The Importance of Grounding, Feb. 16, 2018 (Year: 2018).*

(Continued)

*Primary Examiner* — Linda C Dvorak
*Assistant Examiner* — Nicholas S Borsch
(74) *Attorney, Agent, or Firm* — Bond, Schoeneck & King, PLLC; David L. Nocilly

(57) ABSTRACT

A docking system for electrosurgical equipment where a first docking interface is a recess in the housing of a smoke evacuator and a second docking interface is a raised portion of an electrosurgical unit. The first and second docking interfaces have corresponding ground, power, and communication contacts, so that the two devices can be physically and electrically interconnected by mating the first docking interface with the second docking interface. The first docking interface is on the top of the smoke evacuator and the second docking interface is on the bottom of the electrosurgical unit so that the devices may be stacked and interconnected using a minimum amount of space without the need for cabling.

13 Claims, 5 Drawing Sheets

(52) U.S. Cl.
CPC ................. *A61B 2560/0214* (2013.01); *A61B 2560/0443* (2013.01); *A61B 2560/0456* (2013.01)

(56) References Cited

U.S. PATENT DOCUMENTS

| | | | |
|---|---|---|---|
| 10,363,079 | B2 | 7/2019 | Vacha et al. |
| 10,828,058 | B2 | 11/2020 | Shelton, IV et al. |
| 10,916,415 | B2 | 2/2021 | Karancsi et al. |
| 2004/0177380 | A1* | 9/2004 | Hamel ................... H04N 7/163 |
| | | | 348/E5.002 |
| 2005/0004559 | A1* | 1/2005 | Quick .................... A61B 10/02 |
| | | | 606/1 |
| 2007/0066970 | A1* | 3/2007 | Ineson .............. A61B 18/1206 |
| | | | 606/1 |
| 2010/0069939 | A1* | 3/2010 | Konishi ................. A61B 90/98 |
| | | | 606/169 |
| 2012/0316588 | A1 | 12/2012 | Andreas et al. |
| 2020/0081585 | A1* | 3/2020 | Petre ...................... A61B 34/35 |

FOREIGN PATENT DOCUMENTS

| | | | |
|---|---|---|---|
| JP | 2010-110617 | A2 | 5/2010 |
| KR | 10-2002-0064861 | A | 8/2002 |

OTHER PUBLICATIONS

JP Office Action, App. No. 2021-549663, dated Sep. 13, 2022, pp. 1-10.

International Search Report Form PCT/ISA/210, International Application No. PCT/US2020/019821, pp. 1-10, Dated Jun. 12, 2020.

KR Office Action, App. No. 10-2021-7029202, pp. 1-5, dated Jun. 27, 2023.

* cited by examiner

MODULAR DOCKING SYSTEM FOR ELECTROSURGICAL EQUIPMENT

CROSS-REFERENCES TO RELATED APPLICATIONS

This application is a national stage application under 35 U.S.C. 371 based on international patent application PCT/US20/19821 filed on Feb. 26, 2020, which claims priority to U.S. Provisional Patent Application Ser. No. 62/810,486 filed on Feb. 26, 2019.

BACKGROUND OF THE INVENTION

1. Field of the Invention

The present invention relates to surgical systems and, more specifically, to a system for interconnecting electrosurgical systems to reduce complexity and optimize space.

2. Description of the Related Art

While the addition of innovative and novel technology is needed and desired within the operating room, logistical issues, such as space and power constraints, often arise and can inhibit the introduction of new technology. For example, new modules or devices can take up valuable space within the operating room. In addition, operating rooms may also have a limited number of power outlets in a limited number of locations, resulting in a user having to place devices in non-ideal locations, which can become a safety hazard.

As an example, smoke evacuators used in combination with electrosurgical systems and are typically large modules that require a dedicated power connection. Additionally, smoke evacuators must be positioned relatively close to the electrosurgical unit (ESU) so that the devices can communicate with each other through communication area network (CAN) cables. As a result, there is a need in the field for an approach that allows for multiple systems to be interconnected for power, grounding and communication, thereby reducing complexity and minimizing logistical issues.

BRIEF SUMMARY OF THE INVENTION

The present invention provides for a reduced footprint and less cabling in an operating room using a docking system having a first docking interface comprising a recess in a first housing associated with a first electrosurgical device, wherein the recess includes a first set of electrical contacts extending thereacross and a second docking interface comprising a raised portion in a second housing associated with a second electrosurgical device, wherein the raised portion includes a first set of electrical contacts extending thereacross. The recess is configured to receive the raised portion therein when the first docking interface and second docking interface are positioned together so that the first set of electrical contacts are coupled to and in electrical communication with the second set of electrical contacts. The first set of electrical contacts are arranged linearly across the recess and the second set of electrical contacts are arranged linearly across the raised portion. The first electrosurgical device may be a smoke evacuator, while the second electrosurgical device may be an electrosurgical unit. The first set of electrical contacts are positioned on an upper surface the smoke evacuator, and the second set of electrical contacts are positioned on a lower surface of the electrosurgical unit so that the devices are interconnected by stacking the electrosurgical unit on the smoke evacuator. The first set of electrical contacts and the second set of electrical contacts each comprise a pair of ground contacts, a pair of power contacts, and a series of communication contacts so that the smoke evacuator can powered by the electrosurgical unit and the smoke evacuator will be in communication with the electrosurgical unit via the first docking interface and the second docking interface. The first docking interface extends transversely across an upper surface of the housing of the smoke evacuator and the second docking interface extends transversely across a lower surface of the housing of the electrosurgical unit. The upper surface of the housing of the smoke evacuator may include a third docking interface comprising a recess that corresponds to a fourth docking interface comprising a raised portion on the upper surface of the smoke evacuator that can be received by the recess of the third docking interface. The first docking interface may thus extend across a front portion of the smoke evacuator, the third docking interface may extend across a rear portion of the smoke evacuator, the second docking interface may extend across a front portion of the electrosurgical unit, and the fourth docking interface may extend across a rear portion of the electrosurgical unit.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
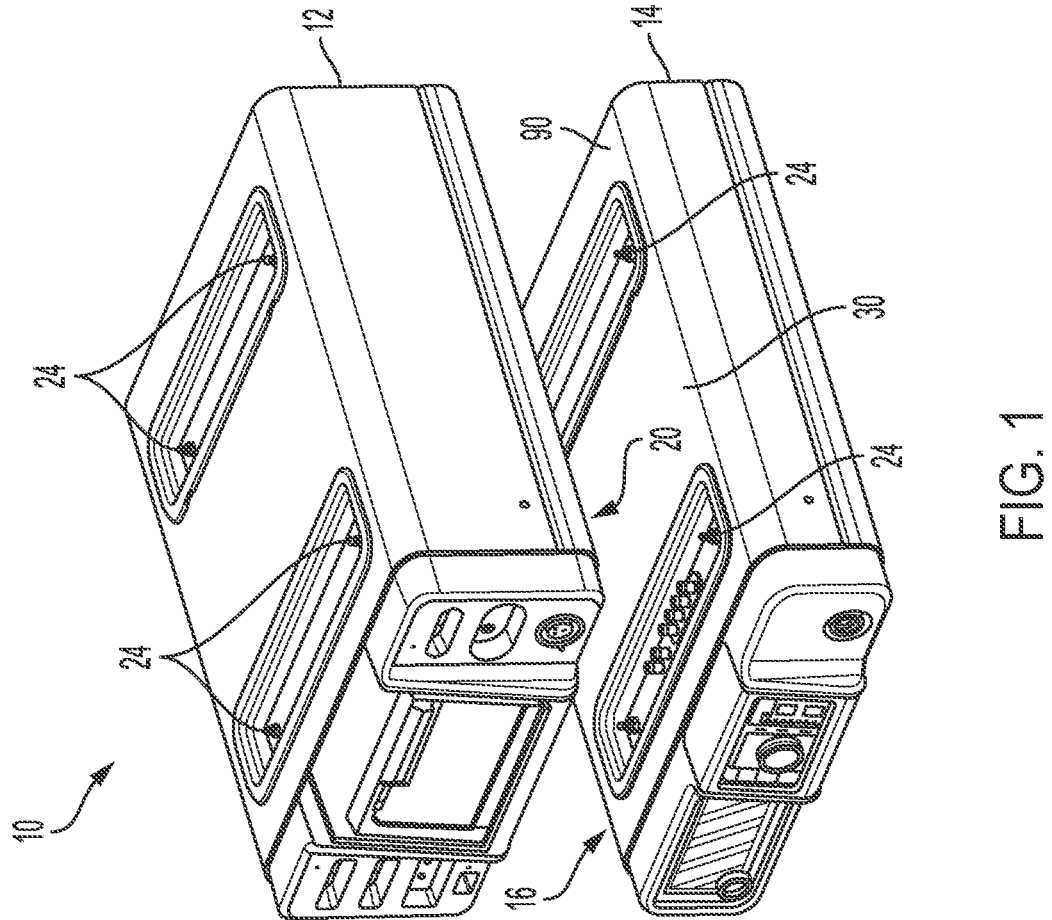
FIG. 1 is a perspective view of a modular interconnection system for electrosurgical equipment according to the present invention.

Referring to the figures, wherein like numeral refer to like parts throughout, there is seen in FIG. 1 an electrosurgical system 10 having two or more interconnected modules, shown as an electrosurgical unit 12 and a smoke evacuator 14. Electrosurgical unit 12 and smoke evacuator 14 are interconnected using an upwardly facing docking interface 16 of smoke evacuator 14 that mates with a corresponding downwardly docking interface 20 of electrosurgical unit 12.

Figure 2:
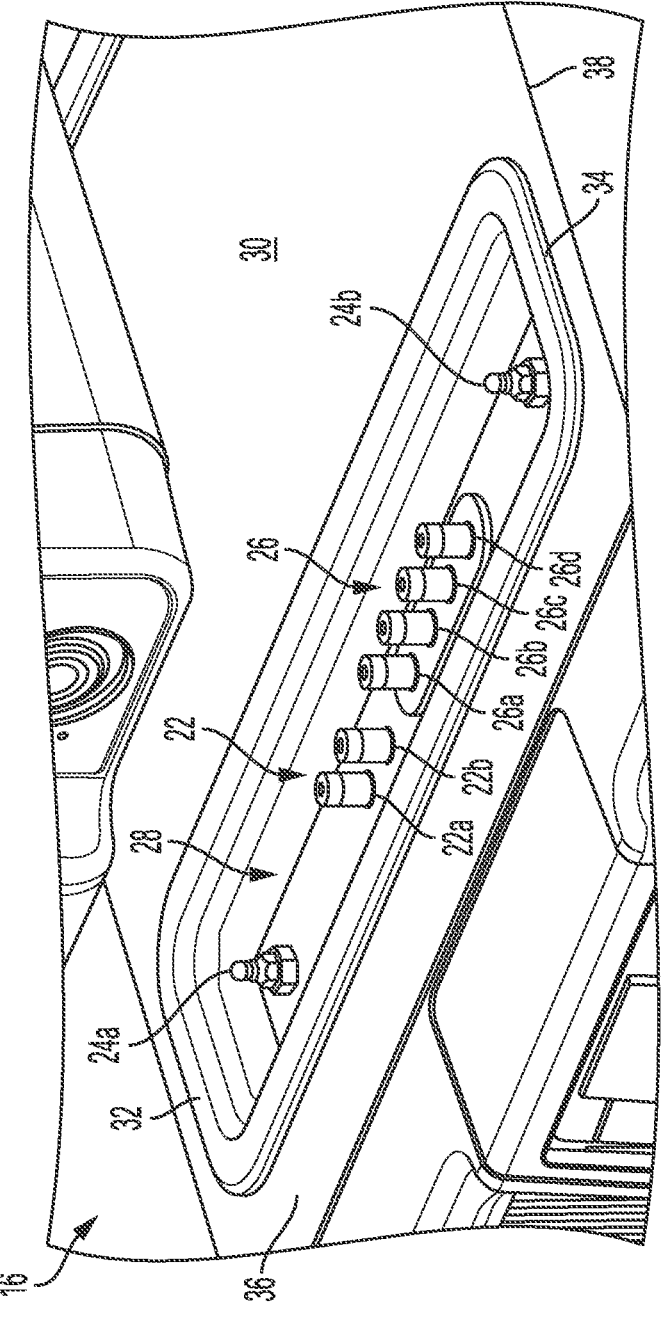
FIG. 2 is a perspective view of a modular docking interface for a smoke evacuator according to the present invention.
Figure 3:
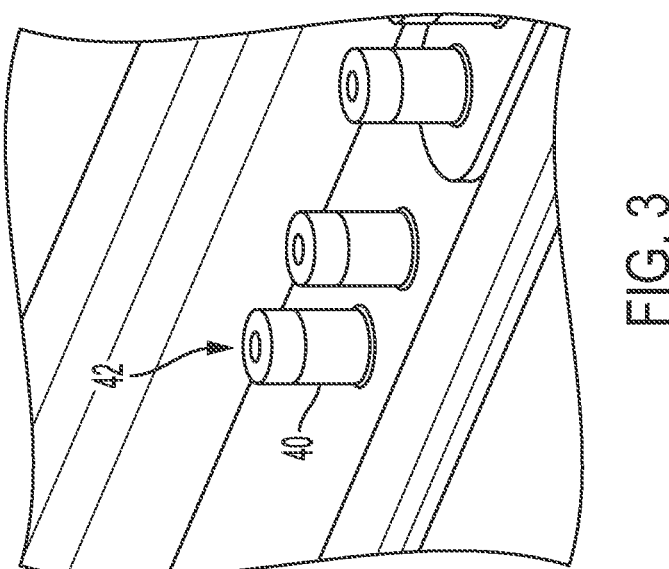
FIG. 3 is a perspective of electrical interconnectors in modular docking interface for a smoke evacuator according to the present invention.

Referring to FIG. 2, docking interface 16 includes a series of power connectors 22, ground studs 24, and communication ports 26, shown as male style connectors positioned within a recessed portion 28 of the housing 30 of smoke evacuator 14. More specifically, docking interface 16 comprises a pair of ground studs 24a and 24b positioned at opposing ends 32 and 34 of recessed portion 28. Recessed portion 28 extends transversely across a forward portion 36 of the upper surface 38 of housing 30. Ground studs 24a and 24b may comprise conventional banana jack plugs that provide electrical connectivity as well as structural coupling. A pair of power connectors 22a and 22b and a series of communication ports 26a, 26b, 26c, and 26d, are positioned and extend between ground studs 24 and 24a and within recessed portion 28. Referring to FIG. 3, power connectors 22a and 22b and a series of communication ports 26a, 26b, 26c, and 26d may comprise cylindrical posts 40 that extend outwardly and upwardly from housing 30, wherein each post 40 defines an inner cavity 42 having electrical contacting faces therein as is conventionally known for electronic interconnection.

Power connectors 22a and 22b, ground studs 24 and 24a, and communication ports 26a, 26b, 26c, and 26d are arranged linearly and extend transversely across forward portion 36 of housing 30. This orientation provides struc- tural stability to the interconnection between electrosurgical unit 12 and smoke evacuator 14 as well as electrical con- nectivity when electrosurgical unit 12 and smoke evacuator 14 are interconnected. The orientation also allows for easy interconnection in the field and ensure that electrosurgical unit 12 and smoke evacuator 14 are aligned in a condensed footprint to minimize the amount of space needed for electrosurgical unit 12 and smoke evacuator 14.

Figure 4:
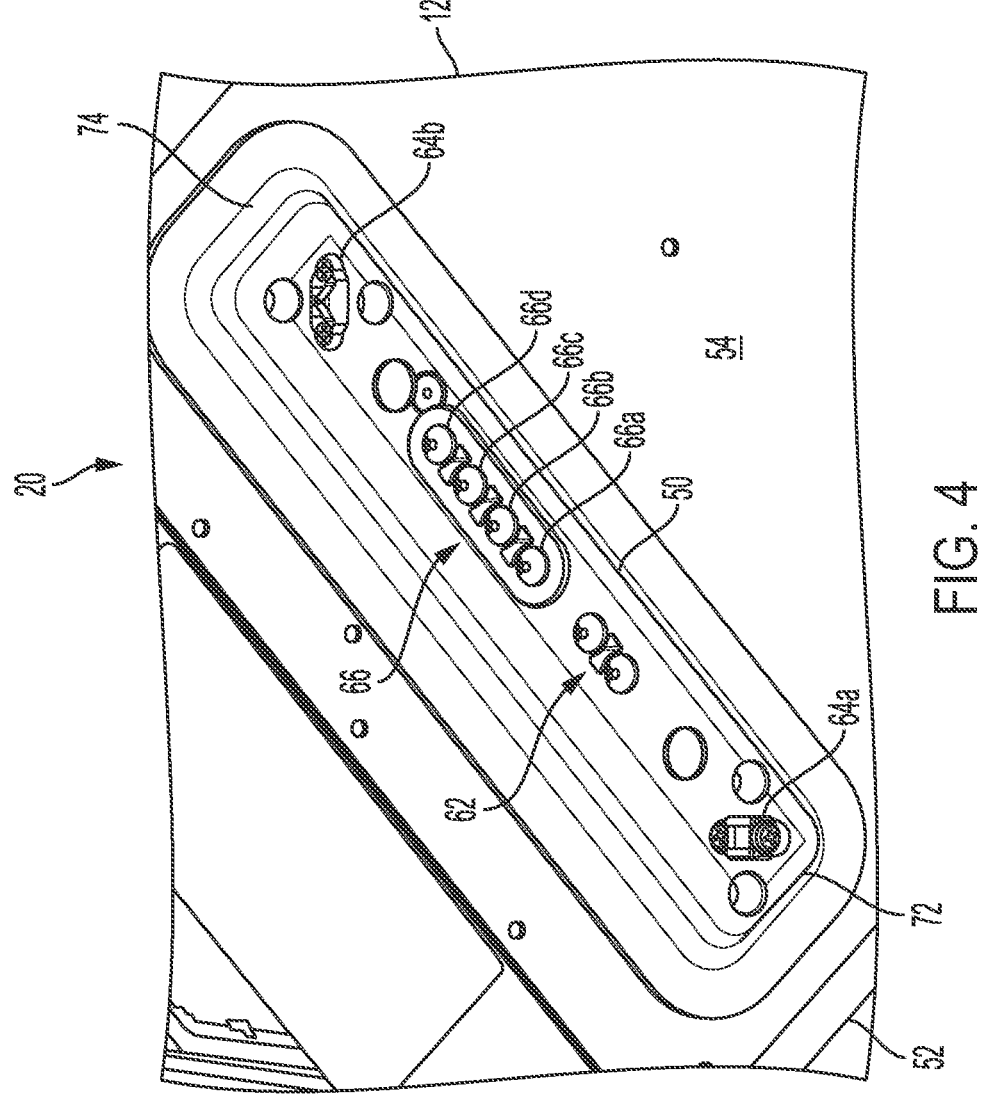
FIG. 4 is a perspective view of a modular docking interface for an electrosurgical unit according to the present invention.

Referring to FIG. 4, docking interface 20 of electrosur- gical unit 12 comprises a raised portion 50 relative to a housing 54 of electrosurgical unit 12. Raised portion 50 extends downwardly from a forward portion 52 of the lower surface of housing 54. The geometry of docking interface 20 corresponds to the geometry of docking interface 16 so that docking interface 20 may be received stably within docking interface 16. For example, docking interface 16 is shown as generally rectangular with a slight taper and radius defining the perimeter of docking interface 16. Docking interface 20 has a corresponding rectangular shape with a slight taper and radius so that docking interface 16 and docking interface 20 can be easily positioned by a user in an interfacing relation- ship and so that when docking interface 20 is seated with docking interface 16, there is contact between the rectan- gular surfaces to provide structural stability between elec- trosurgical unit 12 and a smoke evacuator 14 as they are stacked together.

Docking interface 20 includes series of power connectors 62, ground stud receivers 64a and 64b, and communication ports 46, shown in FIG. 4 as female connectors positioned within raised portion 50 of housing 54 of electrosurgical unit 12. In the example of banana jack plugs as ground studs 24a and 24b, ground stud receivers 64a and 64b may comprise banana jack sockets. As with docking interface 26, docking interface 20 includes a pair of ground stud receivers 64a and 64b positioned at opposing ends 72 and 74 of raised portion 50.

Figure 5:
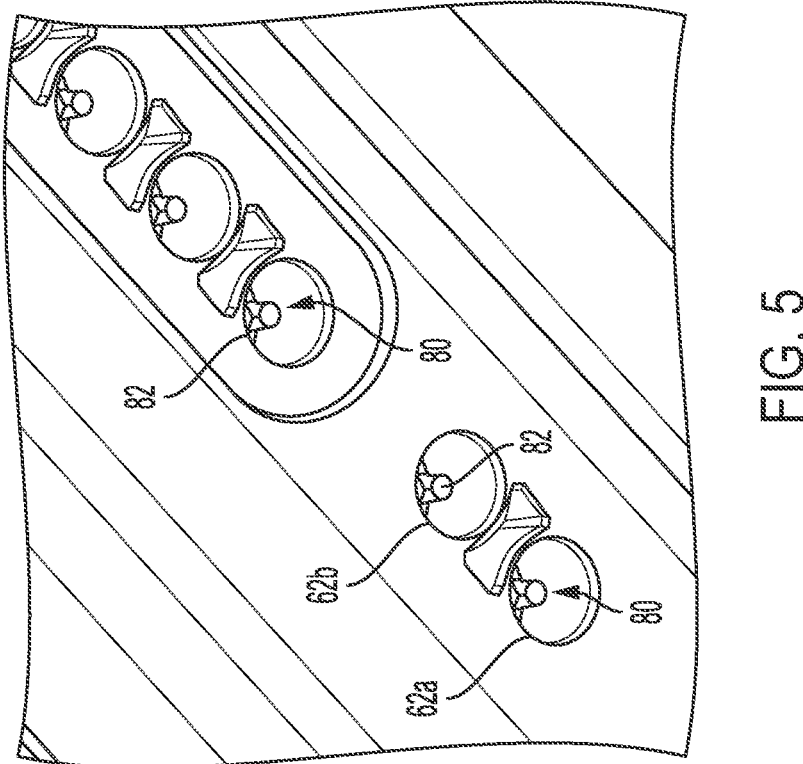
FIG. 5 is a perspective of electrical interconnectors in modular docking interface for an electrosurgical unit according to the present invention.

As seen in FIG. 5, power connectors 62a and 62b and a series of communication ports 66a, 66b, 66c, and 66d may comprise cylindrical receptacles 80 extending inwardly into housing 54 and having a contact pins 82 supported therein for electrical engagement with inner cavities 42 of power connectors 22a and 22b and communication ports 26a, 26b, 26c, and 26d.

Power connectors 62, ground connectors 64, and com- munication ports 66 and positioned to engage power con- nectors 22, ground studs 24, and communication connectors 26 and provide for electrical continuity therebetween when smoke evacuator 14 is positioned on electrosurgical unit 12 so that docking interface 20 is received within docking interface 16. As a result, smoke evacuator 14 can be powered from electrosurgical unit 12 and be placed into electrical communication therewith without the need for an external power cable or a communication interface cable. Instead, simply positioning smoke evacuator 14 on top of electro- surgical unit 12 with provide for power and communication interconnectivity. The connection ports and grounding studs also act to hold the modules together, so they do not come apart unless the user wants to take them apart. The inter- facing of power connectors 62, ground connectors 64, and communication ports 66 with power connectors 22, ground stud receivers 24, and communication ports 26 also helps hold the modules together.

As seen in FIG. 1, smoke evacuator 14 may include an additional receptacle 16 positioned in rear portion 90 that includes additional ground contacts 24. Similarly, electro- surgical unit 12 may include an additional docking interface 20 containing just ground connectors 24 positioned on a rear portion of the downwardly surface. As further seen in FIG. 1, additional upwardly facing docking interfaces 16 may be provided on an upper surface of electrosurgical unit 12 for interconnection to other operating room equipment outfit- ting with docking interfaces according to the present inven- tion. It should be recognized that the docking interfaces of the present invention could be reversed, i.e., the recessed and raised portions reverses, or the positioning of the electrosurgical unit 12 and smoke evacuator 14 reversed with the docking interfaces reverses accordingly.

What is claimed is:

1. A docking system for electrosurgical equipment, com- prising:

a first electrosurgical device having a first housing and a first docking interface comprising a recess that is formed by a first surface of the first housing to include a first taper and a first radius defining the perimeter of the first docking interface and extends transversely across a forward portion of the first housing, wherein the recess includes a first set of electrical contacts extending linearly and transversely thereacross;

a second electrosurgical device having a second housing and a second docking interface comprising a raised portion that is formed by a second surface of the second housing to include a second taper and a second radius defining the perimeter of the second docking interface and extends transversely across a forward portion of the second housing, wherein the raised portion includes a second set of electrical contacts extending linearly and transversely thereacross;

wherein the recess is configured to have a corresponding geometry to the raised portion to receive the raised portion therein in an interfering relationship with the recess and the raised portion in contact with the first taper and the first radius matching the second taper and the second radius, and so that the first set of electrical contacts are coupled to and in electrical communication with the second set of electrical contacts when the first docking interface and second docking interface are positioned together;

wherein the first electrosurgical device comprises one of an electrosurgical generator and a smoke evacuator and the second electrosurgical device comprises the other of the electrosurgical generator and the smoke evacu- ator and wherein the first set of electrical contacts and the second set of electrical contacts provide for interconnected power, grounding and communications between the first electrosurgical device and the second electrosur- gical device such that one of the first electrosurgical device and the second electrosurgical device can power the other of the first electrosurgical device and the second electrosurgical device and the first electrosurgical device through the first docking interface and the second docking interface, one of the first electrosurgical device and the second electrosurgical device can ground the other of the first electrosurgical device and the second electrosurgical device and the first electrosurgical device through the first docking interface and the second docking interface, and the second electrosurgical device can communicate with each other through the first docking interface and the second docking interface.

2. The docking system of claim 1, wherein the first electrosurgical device comprises the smoke evacuator.

3. The docking system of claim 2, wherein the first set of electrical contacts are positioned on an upper surface the smoke evacuator.

4. The docking system of claim 3, wherein the second electrosurgical device comprises the electrosurgical generator.

5. The docking system of claim 4, wherein the second set of electrical contacts are positioned on a lower surface of the electrosurgical generator.

6. The docking system of claim 5, wherein the first set of electrical contacts and the second set of electrical contacts each comprise a pair of ground contacts, a pair of power contacts, and a series of communication contacts.

7. The docking system of claim 6, wherein the smoke evacuator receives power from the electrosurgical generator via the first docking interface and the second docking interface.

8. The docking system of claim 7, wherein the smoke evacuator is in communication with the electrosurgical generator via the first docking interface and the second docking interface.

9. The docking system of claim 8, wherein the first docking interface extends transversely across an upper surface of the housing of the smoke evacuator.

10. The docking system of claim 9, wherein the second docking interface extends transversely across a lower surface of the housing of the electrosurgical generator.

11. The docking system of claim 10, wherein the upper surface of the housing of the smoke evacuator includes a third docking interface comprising a recess.

12. The docking system of claim 11, wherein the lower surface of the housing of the electrosurgical generator includes a fourth docking interface comprising a raised portion that can be received by the recess of the third docking interface.

13. The docking system of claim 12, wherein the first docking interface extends across a front portion of the smoke evacuator, the third docking interface extends across a rear portion of the smoke evacuator, the second docking interface extends across a front portion of the electrosurgical generator, and the fourth docking interface extends across a rear portion of the electrosurgical generator.

* * * * *